US008808203B2

(12) United States Patent
Czarnek

(10) Patent No.: US 8,808,203 B2
(45) Date of Patent: Aug. 19, 2014

(54) CAPACITIVE UTERINE CONTRACTION SENSOR

(75) Inventor: Robert Czarnek, Johnstown, PA (US)

(73) Assignee: General Electric Company, Schenectady, NY (US)

( * ) Notice: Subject to any disclaimer, the term of this patent is extended or adjusted under 35 U.S.C. 154(b) by 936 days.

(21) Appl. No.: 12/389,795

(22) Filed: Feb. 20, 2009

(65) Prior Publication Data

US 2009/0163795 A1 Jun. 25, 2009

Related U.S. Application Data

(63) Continuation of application No. 10/524,984, filed as application No. PCT/US03/26057 on Aug. 19, 2003, now abandoned.

(60) Provisional application No. 60/404,808, filed on Aug. 19, 2002.

(51) Int. Cl.
*A61B 5/04* (2006.01)
*A61B 5/00* (2006.01)

(52) U.S. Cl.
CPC .................................... *A61B 5/4356* (2013.01)
USPC .......................................................... 600/591

(58) Field of Classification Search
USPC ............ 600/591, 390, 587, 562; 73/718, 780, 73/862.626; 361/283.1; 604/167.01–167.06
See application file for complete search history.

(56) References Cited

U.S. PATENT DOCUMENTS 3,577,883 A * 5/1971 Werner ........................... 73/768
3,806,471 A   4/1974 Mitchell
3,913,563 A   10/1975 Ball
4,158,217 A * 6/1979 Bell ............................ 361/283.4
4,178,621 A * 12/1979 Simonelic et al. .......... 361/283.4
4,193,009 A * 3/1980 Durley, III ................ 310/323.19
4,320,667 A * 3/1982 Forrester et al. .......... 73/862.626
4,422,125 A * 12/1983 Antonazzi et al. .......... 361/283.3
4,503,705 A   3/1985 Polchaninoff
4,617,606 A * 10/1986 Shak et al. .................. 361/283.4
4,785,822 A   11/1988 Wallace
4,873,986 A   10/1989 Wallace
4,873,990 A   10/1989 Holmes et al.
4,909,263 A   3/1990 Norris
4,935,841 A * 6/1990 Jonsson et al. ............. 361/283.4

(Continued)

FOREIGN PATENT DOCUMENTS

JP          10170543 A  *  6/1998  ............ G01P 15/125

*Primary Examiner* — Sean Dougherty
*Assistant Examiner* — Michael C Stout
(74) *Attorney, Agent, or Firm* — Andrus Intellectual Property Law, LLP

(57) ABSTRACT

A capacitive uterine contraction sensor includes an insulating substrate, a first electrode disposed on one side of the substrate, and a second electrode positioned on the first side of the substrate in a spaced relation to the first electrode. The second electrode is configured to move toward or away from the first electrode. The sensor may also include a conductive standoff sandwiched between the substrate and the second electrode for maintaining the second electrode in spaced relation to the first electrode. The conductive standoff is electrically coupled to the second electrode and electrically isolated from the first electrode. Alternatively, the second electrode may include a spring mechanism used in conjunction with a standoff to maintain the second electrode in spaced relation to the first electrode. The spring mechanism is electrically isolated from the first electrode and enables the second electrode to move toward or away from the first electrode.

17 Claims, 8 Drawing Sheets

(56) References Cited

U.S. PATENT DOCUMENTS

| | | | |
|---|---|---|---|
| 4,942,882 A | 7/1990 | Bellinson | |
| 4,944,307 A | 7/1990 | Hon et al. | |
| 4,949,730 A | 8/1990 | Cobben et al. | |
| 4,953,563 A | 9/1990 | Kaiser et al. | |
| 4,966,152 A | 10/1990 | Gang et al. | |
| 4,966,161 A | 10/1990 | Wallace et al. | |
| 4,989,615 A | 2/1991 | Hochberg | |
| 5,140,992 A | 8/1992 | Zuckerwar et al. | |
| 5,347,867 A * | 9/1994 | Pangerl | 73/514.32 |
| 5,525,955 A * | 6/1996 | Tonogai et al. | 338/185 |
| 5,634,476 A * | 6/1997 | Orkin et al. | 600/588 |
| 5,672,850 A * | 9/1997 | Liu | 177/210 C |
| 5,742,167 A * | 4/1998 | Haynes | 324/671 |
| 5,836,063 A * | 11/1998 | Hegner et al. | 29/25.42 |
| 5,869,751 A * | 2/1999 | Bonin | 73/105 |
| 5,902,933 A * | 5/1999 | Bingo et al. | 73/724 |
| 5,954,850 A * | 9/1999 | Bernot et al. | 65/60.1 |
| 6,091,029 A * | 7/2000 | Lee | 177/210 C |
| 6,145,384 A * | 11/2000 | Ikeda et al. | 73/780 |
| 6,388,452 B1 * | 5/2002 | Picciotto | 324/663 |
| 6,604,425 B1 * | 8/2003 | Hsu et al. | 73/718 |
| 6,606,911 B2 * | 8/2003 | Akiyama et al. | 73/718 |
| 6,631,645 B1 * | 10/2003 | Satou et al. | 73/718 |
| 6,820,493 B1 * | 11/2004 | Bonin | 73/780 |
| 6,823,747 B2 * | 11/2004 | Hasegawa et al. | 73/862.52 |
| 6,829,953 B2 * | 12/2004 | Ishiguro et al. | 73/862.52 |
| 6,848,318 B2 * | 2/2005 | Gerst et al. | 73/715 |
| 7,046,497 B1 * | 5/2006 | Bonin | 361/290 |
| 7,451,654 B2 * | 11/2008 | Maiorana et al. | 73/718 |
| 7,802,374 B1 * | 9/2010 | Chen et al. | 33/784 |
| 2002/0011114 A1 * | 1/2002 | Miyashita et al. | 73/718 |
| 2002/0135440 A1 * | 9/2002 | Ryhanen et al. | 333/185 |
| 2002/0151816 A1 * | 10/2002 | Rich et al. | 600/547 |
| 2003/0019299 A1 * | 1/2003 | Horie et al. | 73/718 |
| 2003/0187370 A1 * | 10/2003 | Kodama | 600/591 |
| 2005/0223811 A1 * | 10/2005 | Bonin | 73/780 |
| 2007/0180924 A1 * | 8/2007 | Warren et al. | 73/780 |

\* cited by examiner

CAPACITIVE UTERINE CONTRACTION SENSOR

CROSS REFERENCE TO RELATED APPLICATIONS

This application claims priority to currently pending U.S. patent application Ser. No. 10/524,984 filed Jan. 11, 2006.

FIELD OF THE INVENTION

This invention relates generally to fetal monitoring apparatuses and, more particularly, to an apparatus for sensing uterine activity, in particular, contractions.

DESCRIPTION OF THE PRIOR ART

Fetal monitors, which are typically quite sophisticated, are widely used to monitor the uterine activity of pregnant women, as well as the condition of the fetus and the uterus. Analysis of uterine contractions, in conjunction with fetal heart rate, during pregnancy and labor yields significant information concerning the condition of the fetus as well as the advancement of labor. Such monitoring is particularly helpful in so-called difficult pregnancies to systematically evaluate fetal stress, but it is certainly of use in more routine pregnancies as well.

Information of fetal distress will result in prompt remedial action, including a cesarean delivery, both during pregnancy and/or during actual labor. Likewise, early contractions can be treated so as to achieve full-term pregnancies. Examples of currently available fetal monitors include the FetaScan from International Biomedics, Inc., the Corometrics 115, and the Hewlett-Packard 8040A.

Such fetal monitors, however, regardless of their sophistication, require a device or element to actually sense the uterine contractions.

These elements can be intra-uterine or extra-uterine. An example of an intra-uterine sensing element is a catheter which is capable of measuring uterine activity within the uterine cavity itself. Such sensors are disclosed in U.S. Pat. Nos. 4,785,822; 4,873,986; 4,873,990; 4,909,263; 4,942,882; 4,944,307; 4,953,563; and 4,966,161. However, these devices are invasive and therefore they cannot be used for pre-term monitoring.

Other devices, known as tocotonometers, are capable of non-invasively sensing uterine activity and, therefore, are widely used with fetal monitors. Tocotonometers measure the hardness of the abdomen wall, which is an indication of the uterine activity, by various mechanical means. Specifically, tocotonometers include strain gauge elements mounted to an elastic member or are based on LVDT sensors. Tocotonometers are expensive, structurally delicate, i.e., break easily, and are difficult to sanitize between uses. In use, the tocotonometer is held in contact with the abdomen, usually by a belt-like device, in the vicinity of the fundus, i.e., the top of the uterus. The tocotonometer under pre-load by the belt responds with a constant recording level between contractions. The output of the tocotonometer is transmitted to the fetal monitor. Examples of such tocotonometers are manufactured by Huntleigh, Model #447; Corometrics, Model #2260; and Hewlett-Packard, Model #15248A. Other types of mechanical-type sensors for measuring uterine contractions are disclosed in U.S. Pat. Nos. 3,913,563; 4,949,730; 4,966,152; and 4,989,615. Like tocotonometers, these devices are expensive, complicated in construction and use, and difficult to sanitize between uses. The sensor disclosed in U.S. Pat. No. 4,949,730 utilizes a piezoelectric element which cannot measure contractions over a sustained period of time because the charge of the piezoelectric element dissipates quickly, e.g., several seconds.

Accordingly, it is desirable to provide an apparatus for detecting uterine activity which is inexpensive, non-complicated in construction, easy to operate, easy to clean, can be made disposable or reusable, does not decay or electrically drift over time, and/or can be interchanged with presently available fetal monitors. Still other desirable features of the invention will become apparent to those of ordinary skill in the art upon reading and understanding the following detailed description.

SUMMARY OF THE INVENTION

The present invention is directed toward an extra-uterine sensing device for directly measuring changes in pressure brought about by uterine contractions of a wearer. The device includes a circuit board, two electrodes, a gap between the electrodes which is filled by air or some other deformable dielectric material, a device to maintain the gap, and a circuit used to measure changes in capacitance.

The first electrode is held stationary with respect to the base, while the second electrode is allowed to move relative to the first electrode. The relevant movement is enabled through the use of a spring mechanism or the elastic deflection of a non-stationary electrode under an applied load. The change in distance between the electrodes varies the gap and, therefore, the capacitance, between the electrodes. If a higher level of sensitivity or a smaller size is required, the gap can be filled with a dielectric fluid or deformable dielectric material. An electronic circuit connects to the capacitive sensing device and properly scales the change in capacitance and outputs the scaled result to a monitor or like device capable of displaying the desired information regarding the strength of the contraction. A shield eliminating the electrical influence of external objects can be placed around the electrodes to further improve the performance of the device.

A minimum pre-load is applied to the sensing device sufficient to establish a reference level of pressure. Once the reference level is attained, the sensing device instantaneously detects changes in the pressure caused by contractions. The changes in pressure are then converted to a change in capacitance and the change in capacitance is then converted to a non-decaying electrical signal which is monitored.

The device can be held against the uterus through a variety of means. These means include an elastic belt, strap, applying adhesive material to the base of the sensing device, or any like method. The belt would be tightened to apply the minimum level of pre-load to the sensing device. Alternatively, a weight can be adapted to rest upon the outer member to apply more force if the belt does not establish the required minimum level of pre-load. A weight could also be utilized to apply the required minimum level of pre-load if the sensing device is held to the uterus through the use of an adhesive material.

The device can be built as an inexpensive disposable unit or can be used as the sensing element in a permanent multiple-use transducer. In a disposable embodiment, the whole transducer can be formed by the technology used to produce multi-layer printed circuit boards where the fiberglass plate typically used as the structural material of the boards is used as the elastic element of the transducer. A calibration resistor or equivalent component can be added to the assembly to assure repeatability from unit to unit. If the electronic circuit is based on a microprocessor chip, then its memory can be used to store the proper calibration constants.

These and other advantages of the present invention will be understood from the description of the preferred embodiments, taken with the accompanying drawings, wherein like reference numerals represent like elements throughout.

DESCRIPTION OF THE PREFERRED EMBODIMENTS

The present invention will be described with reference to the accompanying figures, where like reference numbers correspond to like elements. It is to be understood that the attached figures and the following specification are for the purpose of describing the invention and are not to be construed as limiting the invention.

Figure 1:
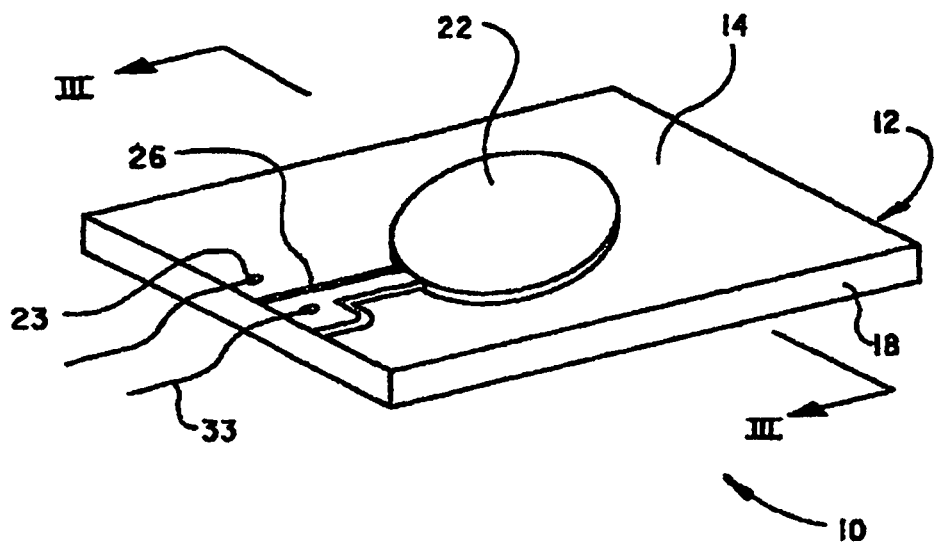
FIG. 1 is a perspective view of a first embodiment of a capacitive sensing element.
Figure 3:
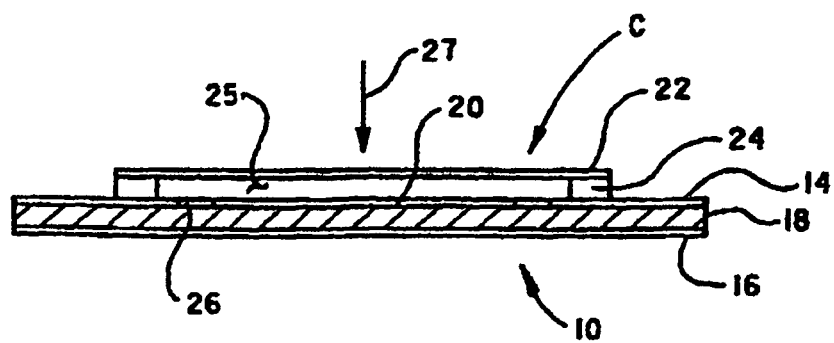
FIG. 3 is a cross-sectional side view of the sensing element taken along lines III-III in FIG. 1.
Figure 2:
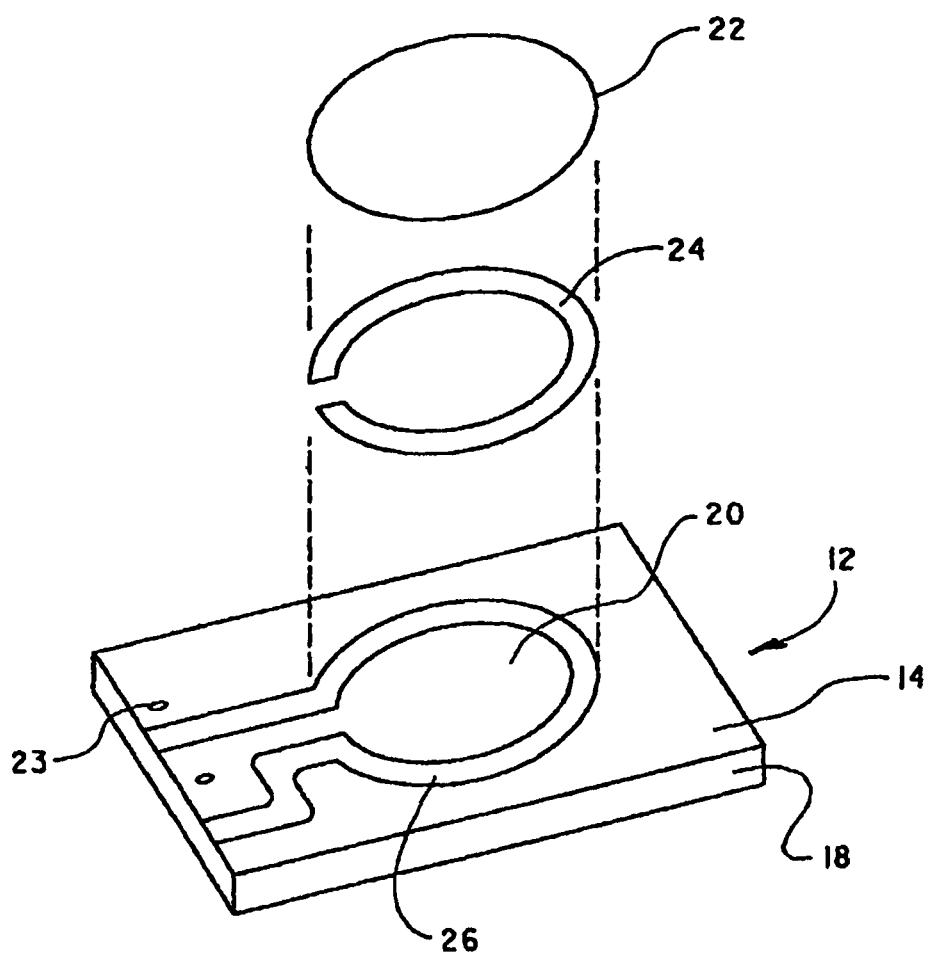
FIG. 2 is an exploded perspective view of the sensing element of FIG. 1.

FIGS. 1-3 are views of a first embodiment capacitive sensing element 10, with FIG. 2 illustrating an exploded view of the component parts thereof. Sensing element 10 includes a printed circuit board 12, having a copper top 14, a copper base 16, and an insulating, e.g., fiberglass, substrate 18. An electrically isolated stationary electrode 20 is defined in copper top 14 by removing, e.g., etching, a suitable portion of copper top 14 to form therein a crevice 26 having as its base an exposed portion of substrate 18. An exemplary thickness of printed circuit board 12 is 1.6 mm, so as to allow for an appropriate thickness of copper top 14, copper base 16 and substrate 18. An electrode 22 is held in spaced relation to stationary electrode 20 by a standoff 24 whereupon a gap 25 is created between electrodes 20 and 22. Desirably, gap 25 is filled with air. However, if greater sensitivity is required, gap 25 can be filled with a dielectric fluid or a deformable dielectric solid material. Desirably, standoff 24 is formed from electrically conductive material. Alternatively, standoff 24 can be formed from any suitable material having an electrically conducting coating thereon. Standoff 24 is configured to be received on copper top 14 in electrical contact herewith and electrically isolated from stationary electrode 20 by crevice 26.

Electrode 22 is electrically connected via standoff 24 to copper top 14 and copper base 16. Copper top 14 and copper base 16 may be connected via any number of suitable means including, but not limited to, a conductively plated through-hole 23. This electrically connected arrangement acts as a ground, and thus forms an electric shield around stationary electrode 20. Desirably, electrode 22 is constructed out of a thin elastic metal plate, such as beryllium-copper or stainless steel. Such a design would assure long-time stability and durability of the product. However, electrode 22 can be formed from any suitable elastic conductive material.

When a force is applied to electrode 22 in the direction of arrow 27 in FIG. 3, electrode 22 will move toward stationary electrode 20. This movement changes the size of gap 25 and, hence, a capacitance of a capacitor C formed by electrodes 20 and 22 held in spaced relation by standoff 24.

Figure 4:
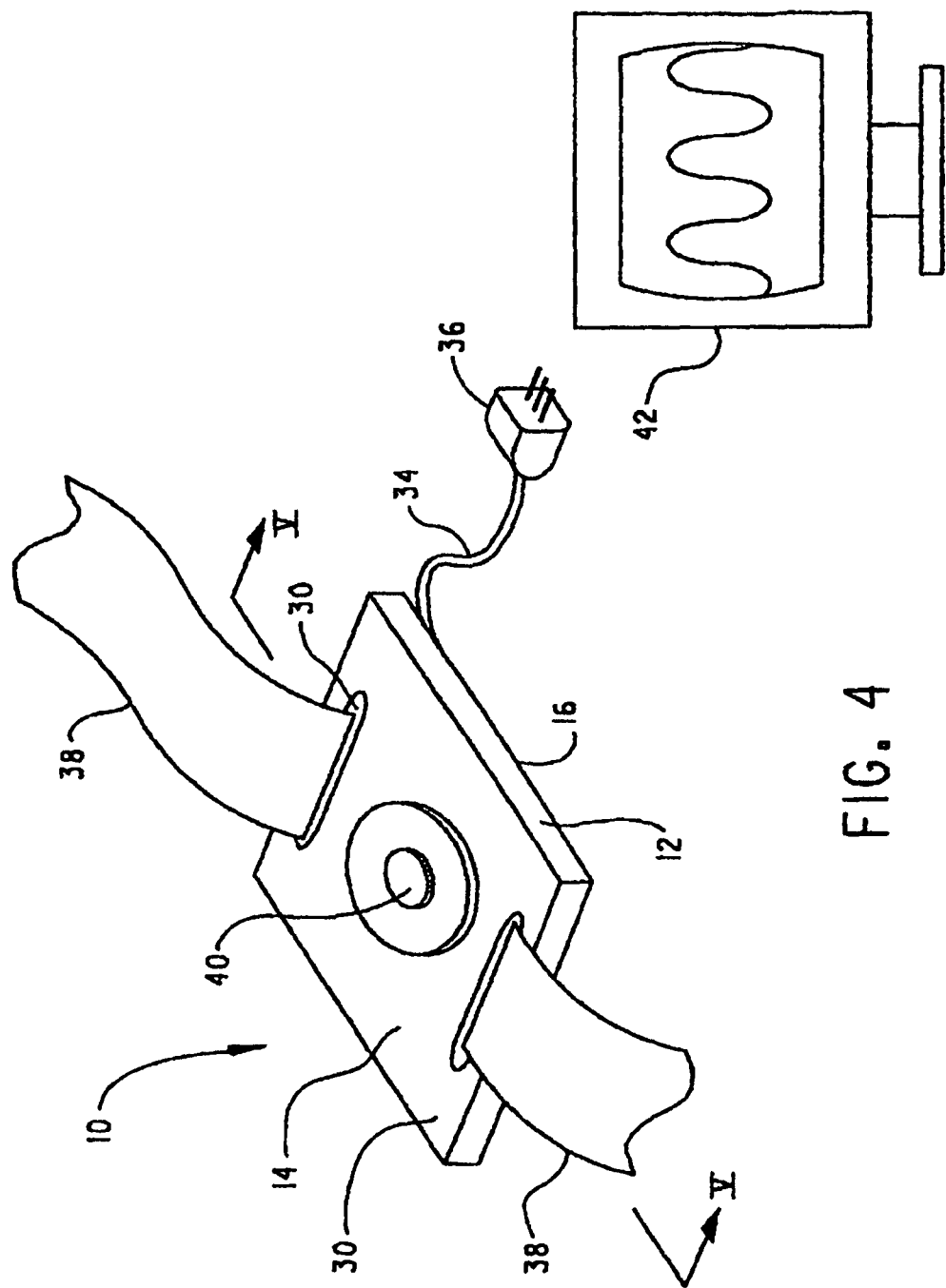
FIG. 4 is a perspective view of the sensing element of FIG. 1 incorporating electronic circuitry.
Figure 5:
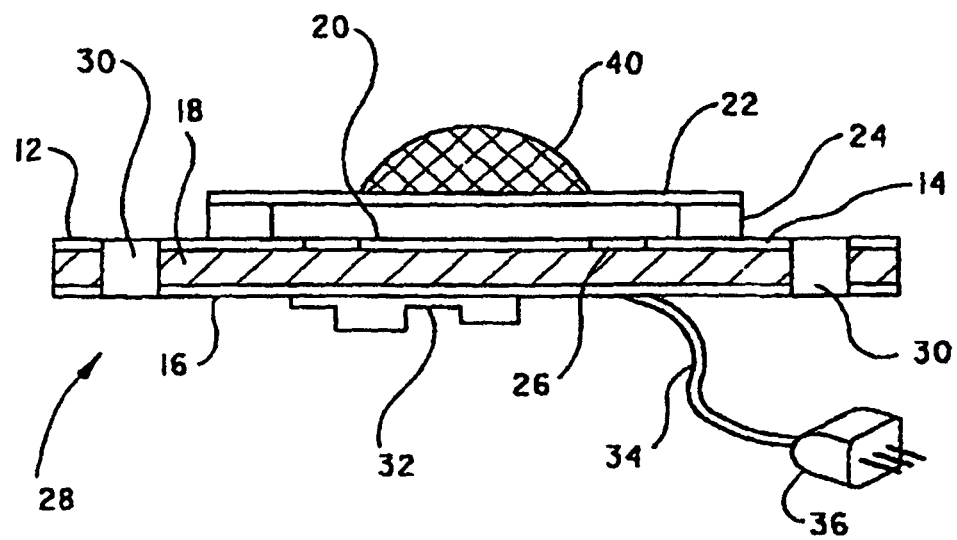
FIG. 5 is a cross-sectional side view of the sensing element of FIG. 4 taken along lines V-V in FIG. 4.
Figure 5:
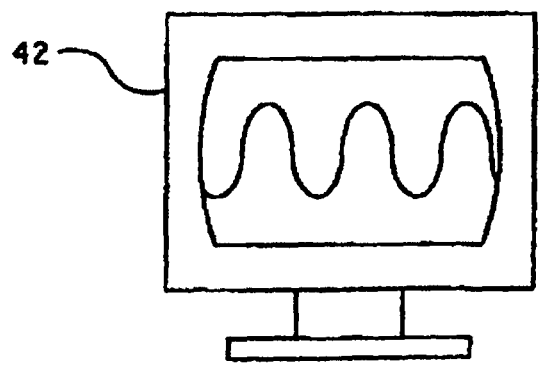

With reference to FIGS. 4 and 5 and with continuing reference to FIGS. 1-3, slots 30 can be formed through substrate 12, copper top 14 and copper base 16 adjacent to sides or edges of substrate 12. A belt 38, e.g., an elastic belt, can be threaded through slots 30 as shown and can be utilized for securing sensing element 10 against a patient's abdomen. It is to be understood, however, that slots 30 and elastic belt 38 serve as exemplary means for securing sensing element 10, and that other means (not shown) exist, including the use of adhesive materials for securing sensing element 10 to a patient.

Alternatively, sensing element 10 may include a load transfer button 40 placed on top of electrode 22 as shown. Load transfer button 40 allows a pre-load to bias electrode 22 toward stationary electrode 20 when elastic belt 38 is tightened around a patient.

Electronic circuitry 32 can be coupled in a suitable manner to a side of substrate 18 having copper base 16 thereon. To this end, a suitable pattern of interconnects (not shown) can be formed, e.g., etched, on copper base 16 in a manner known in the art for receiving electronic circuitry 32. Electronic circuitry 32 converts the capacitance of capacitor C into an electric signal. Where the capacitance of capacitor C changes in response to movement of electrode 22 toward or away from stationary electrode 20, e.g., in response to the onset or end of a uterine contraction, this change causes a change in the electrical signal output by electronic circuitry 32. This change can be output through a cable 34 to a suitable monitoring unit 42 for storage and/or display in an understandable format representing, for example, the rate of contraction and/or other related information. It is to be understood that the electric signal may be communicated to and/or displayed in other ways including, but not limited to, through the use of a wireless transmitter-receiver link. Thus, appropriate modifications known to those having ordinary skill in the art can be made to electronic circuitry 32. This may include adding battery-operated capabilities to sensing element 10.

FIG. 5 shows electronic circuitry 32 located on a side of printed circuit board 12 opposite electrode 22. Alternatively, electronic circuitry 32 can be positioned on the same side of printed circuit board 12 as electrode 22. In yet another alternative, electronic circuitry 32 can be situated entirely off printed circuit board 12, yet still be connected to printed circuit board 12 through any suitable means including, but not limited to, electrical lines 33, as shown in FIG. 1. This alternative may be used when sensing element 10 is considered to be disposable, in that high-cost and reusable components, such as electronic circuitry 32, are offboard. Thus, after disposing of one sensing element 10, electrical lines 33 of another sensing element 10 may then be reattached to the offboard electronic circuitry.

Figure 6:
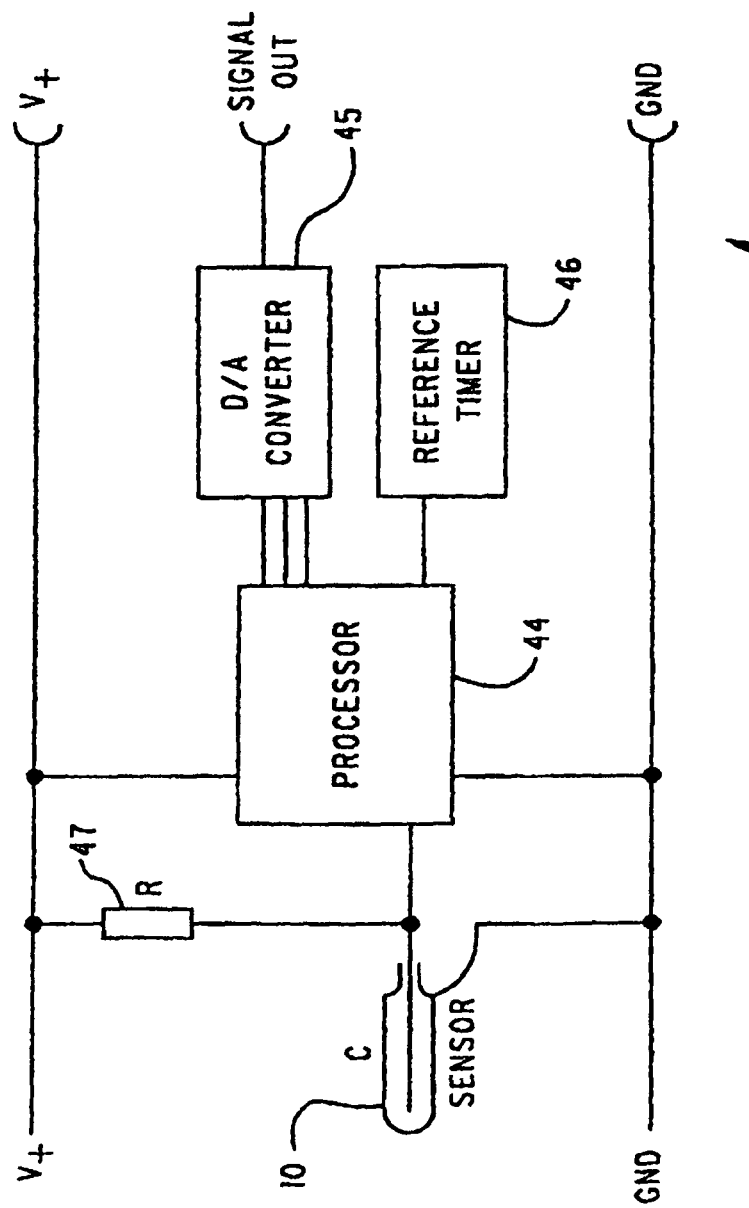
FIG. 6 is a simplified schematic of the electronic circuitry of the sensing element of FIG. 4.
Figure 7:
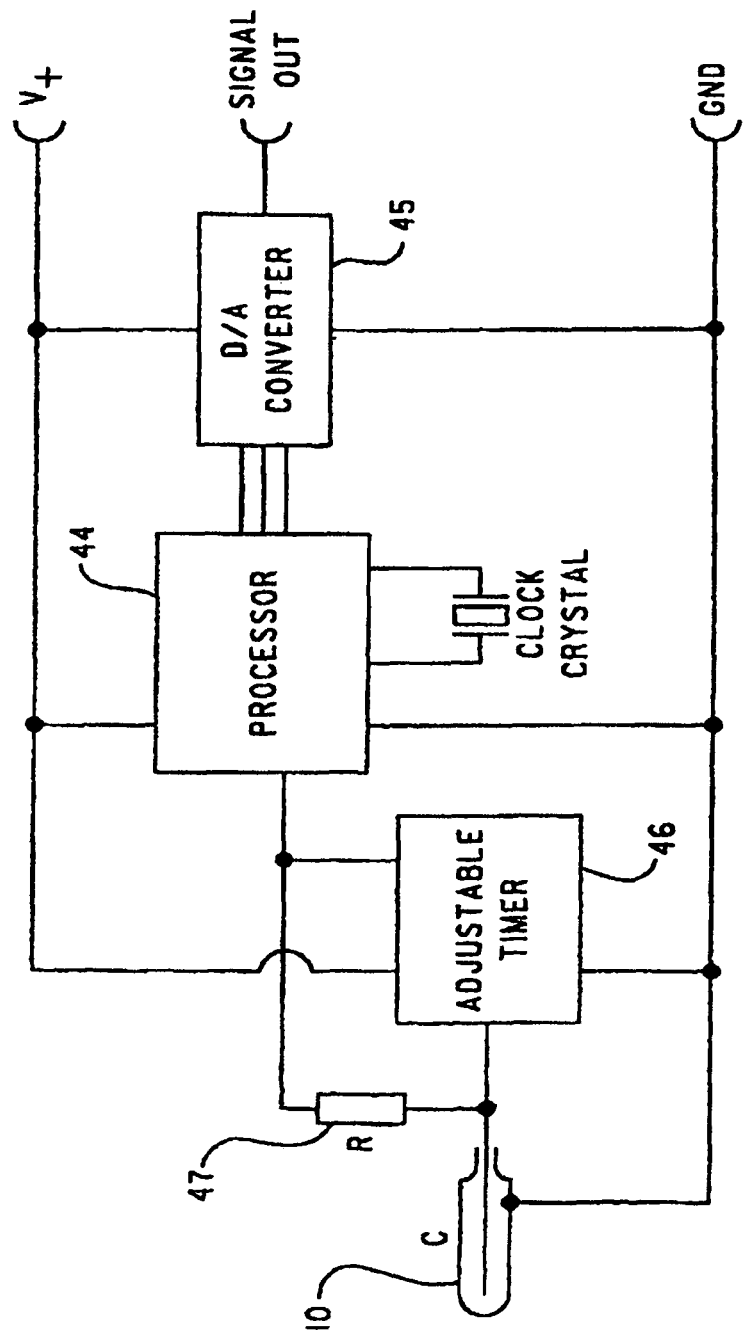
FIG. 7 is an alternate embodiment of the electronic circuitry of the sensing element of FIG. 4.

With reference to FIG. 6 and with continuing reference to FIGS. 1-5, electronic circuitry 32 can include a processor 44, a digital-to-analog converter 45, a reference timer 46, a resistor 47 and capacitor C defined by sensing element 10. In operation, reference timer 46 outputs a timing signal to processor 44. If gap 25 between stationary electrode 20 and electrode 22 varies, the capacitance of sensing element 10 will change whereupon the RC time constant of capacitor C and resistor 47 will also change. Processor 44 is configured to determine the capacitance of sensing element 10 using the RC time constant and the inputted timing signal from reference timer 46. Processor 44 will then output a digital signal related to the determined capacitance, which is transformed into an analog signal by the digital-to-analog converter 45. This analog signal can then be displayed in an understandable format by monitoring unit 42 as contraction related information. It is to be understood that there are, however, several known methods for measuring capacitance which could be used in accordance with the present invention. For example, as shown in FIG. 7, sensing element 10 and resistor 47 can be connected to alter the frequency of a signal output by adjustable frequency timer 46, e.g., a 555 timer, to processor 44, which is operating at a fixed frequency. In this embodiment of electronic circuitry 32, processor 44 is configured to convert the frequency of the signal output by reference timer 46 into a signal indicative of the capacitance of capacitor C.

Figure 8:
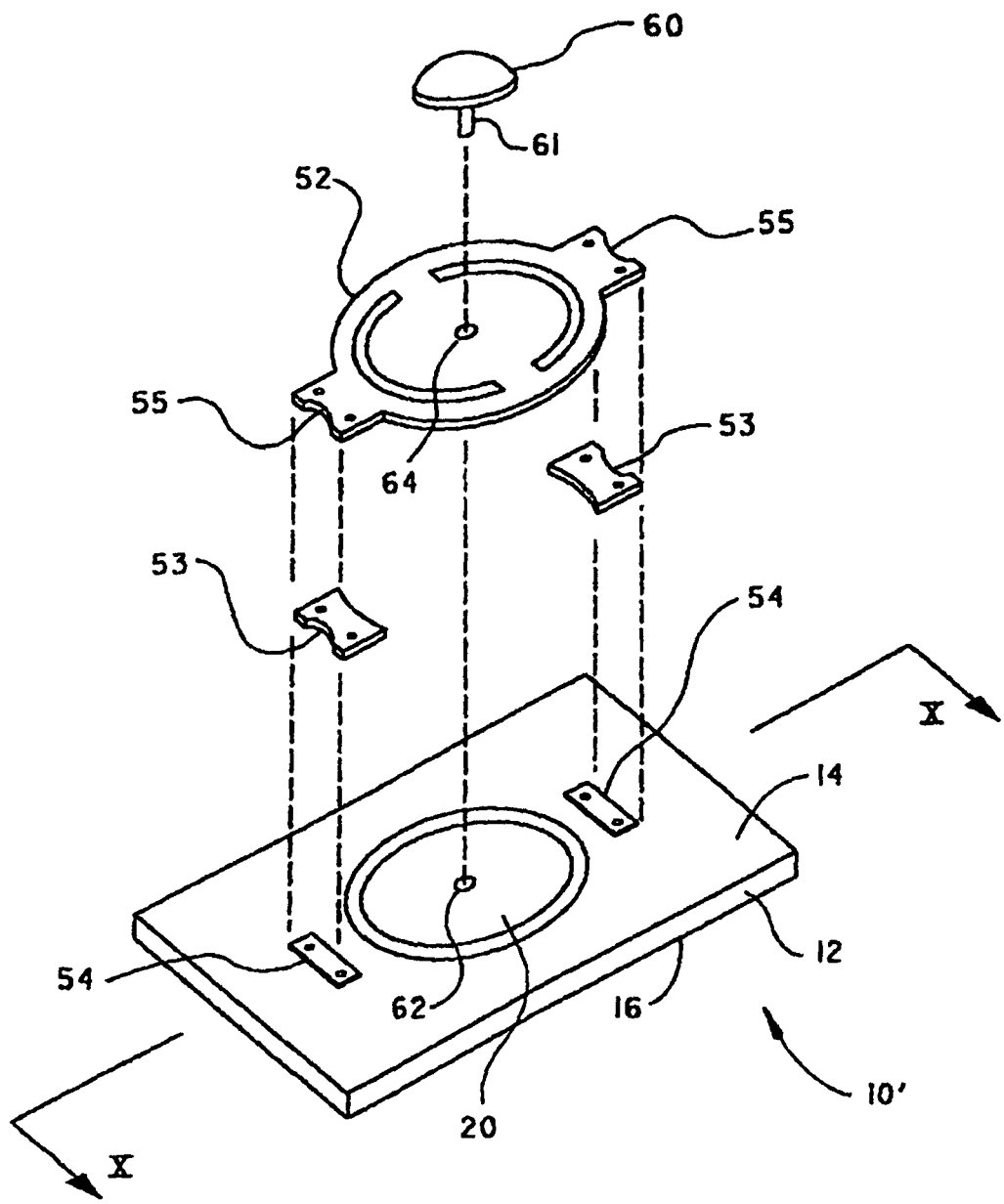
FIG. 8 is an exploded perspective view of a second embodiment of the capacitive sensing element.
Figure 9:
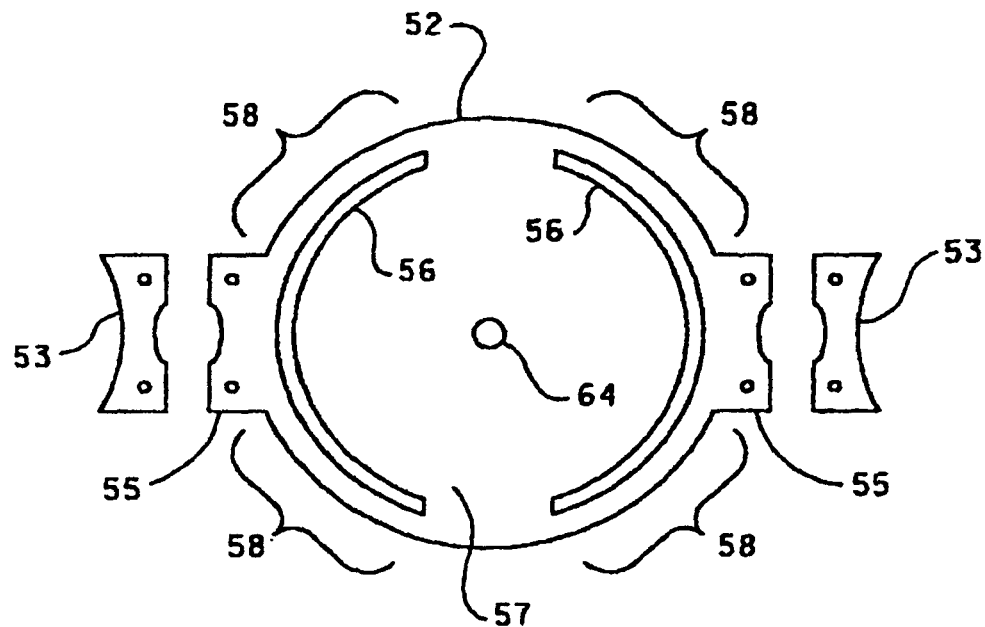
FIG. 9 is top view of a spring mechanism of the second embodiment of the capacitive sensing element of FIG. 8.
Figure 10:
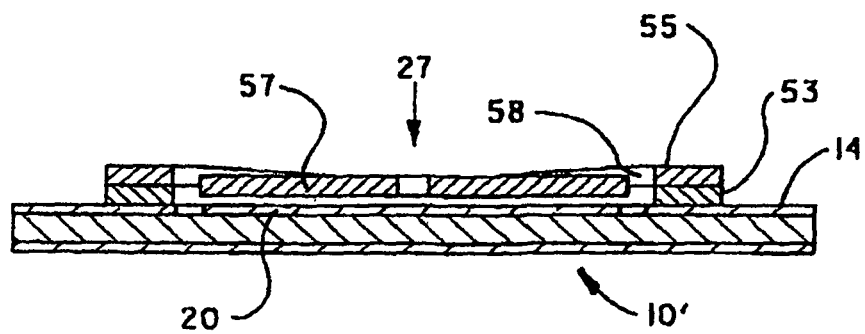
FIG. 10 is a cross-sectional side view of the second embodiment of the capacitive sensing of FIG. 8 taken along lines X-X in FIG. 8.

While first embodiment capacitive sensing element 10 utilizes electrode 22 in combination with standoff 24, a second embodiment capacitive sensing element 10' can utilize an electrode in combination with a spring mechanism. With reference to FIGS. 8-10 and with continuing reference to FIGS. 1-7, the second embodiment capacitive sensing element 10' is shown with additional and substituted components differentiating it from sensing element 10. Essentially, electrode 22 and standoff 24 of capacitive sensing element 10 are not utilized in capacitive sensing element 10'. Instead, sensing element 10' includes an electrode having a body in the form of a disc 52, a plurality of standoffs 53, and a plurality of mounting pads 54. It is to be understood that the body may be of any suitable shape, and is shown herein as a disc for exemplary purposes. Desirably, disc 52 is constructed of beryllium-copper. However, this is not to be construed as limiting the invention since the use of any suitable material such as stainless steel or a copper-clad fiberglass plate is envisioned.

Disc 52 includes tabs 55 extending from opposite sides thereof. Additionally, disc 52 includes channels 56, allowing a central portion 57 of disc 52 to move relative to tabs 55. Thus, the arrangement of channels 54 forms a spring mechanism integrated within disc 52. More specifically, each channel 56 defines a pair of fingers 58, each of which extends away from the adjacent tab 55. The fingers 58 coact to form a spring mechanism that enables central portion 57 to move toward and away from substrate 12 when disc 52 is attached thereto. Each standoff 53 is positioned and secured between tab 55 of disc 52 and one of the mounting pads 54 of printed circuit board 12. This causes disc 52 to be disposed in spaced relation to stationary electrode 20, while enabling disc 52 to be moved toward or away from stationary electrode 20 via the spring mechanism. Specifically, when a force in the direction of arrow 27 is applied to disc 52, the central portion 57 moves toward stationary electrode 20 to the position shown in FIG. 10. When the force is removed, the spring mechanism moves central portion 57 away from stationary electrode 20. It is to be understood that disc 52 is electrically isolated from stationary electrode 20 and is electrically connected to copper top 14 via standoff 53.

Load transfer button 40 that is placed on top of electrode 22, shown in FIG. 4, may also be placed on top of disc 52. Alternatively, a different load transfer button 60 having a stem 61 may be utilized in both sensing element 10 and sensing element 10'. To this end, as shown in FIG. 8, printed circuit board 12 may include a hole 62 that extends through a top surface of stationary electrode 20 and into printed circuit board 12. Additionally, disc 52 includes a centrally situated hole 64. This allows for stem 61 of load transfer button 60 to be received through hole 64 and into hole 62, resulting in load transfer button 60 abutting disc 52. Thus, in operation, a force resulting from uterine contraction applied to load transfer button 60, will cause load transfer button 60 to move disc 52 toward stationary electrode 20. A change in the size of gap 25 between disc 52 and stationary electrode 20 creates a change in capacitance of a capacitor formed by disc 52 and stationary electrode 20 that can be detected and processed by processor 44. It is to be appreciated that hole 62 guides stem 61 and stabilizes load transfer button 60, thereby preventing horizontal movement of disc 52 and ensuring accurate measurements of uterine contractions. If load transfer button 60 is utilized in sensing element 10, then electrode 22 and stationary electrode 20 necessitate appropriate holes for accommodating stem 61 therein.

It is to be understood that the general function and operation of second embodiment capacitive sensing element 10' is similar to that of first embodiment capacitive sensing element 10. Thus, although not explicitly shown, sensing element 10' can include on onboard or remote electronic circuitry 32. The calculation and transmission of the electric signal in electronic circuitry 32 utilized in sensing element 10' is also similar. Additionally, sensing element 10' can be attached to a patient using the same means as described above for sensing element 10.

The invention has been described with reference to the preferred embodiment. Obvious modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A capacitive sensor comprising:
   means for securing the capacitive sensor against an abdomen;
   an insulating substrate;
   a first electrode disposed on a first side of the substrate;
   a second electrode positioned on the first side of the substrate in a spaced relation to the first electrode, at least part of the second electrode configured to move toward or away from the first electrode in response to a uterine contraction of the abdomen; and
   a conductive standoff sandwiched between the substrate and the second electrode for maintaining the second electrode in spaced relation to the first electrode, the conductive standoff electrically coupled to the second electrode and electrically isolated from the first electrode; and
   a conductive sheet on each side of the substrate, wherein:
   the conductive sheets are electrically connected;
   the first electrode is electrically isolated from the conductive sheet on the first side of the substrate; and the second electrode is electrically connected to the conductive sheet on the first side of the substrate via the conductive standoff;
   wherein the conductive sheets in combination with the second electrode and the conductive standoff are configured to form an electric shield around the first electrode.

2. The capacitive sensor of claim 1, wherein the conductive standoff surrounds the first electrode.

3. The capacitive sensor of claim 1, wherein the second electrode comprises a spring mechanism, wherein the spring mechanism is electrically isolated from the first electrode, the second electrode maintained in spaced relation to the first electrode.

4. A capacitive sensor comprising:
- a belt configured to secure the capacitive sensor to an abdomen;
- an insulating substrate having a first side and a second side;
- a first conductive sheet on the first side of the insulating substrate;
- a first electrode disposed on a first side of the substrate, the first electrode being electrically isolated from the first conductive sheet and the first electrode defines a first hole through the first electrode into the insulating substrate;
- a second electrode positioned above the first side of the insulating substrate in a spaced relation to the first electrode, at least part of the second electrode configured to move toward or away from the first electrode, the second electrode defines a second hole through second electrode;
- a conductive standoff sandwiched between the first conductive sheet and the second electrode, the conductive standoff maintains the spaced relation between the first and second electrodes, and the conductive standoff is electrically isolated from the first electrode;
- a load transfer button positioned on a side of the second electrode facing away from the first electrode; and
- a stem that extends from the load transfer button through the second hole in the direction of the first electrode, the stem is received at least partially within the first hole and the first hole guides the stem to prevent horizontal movement of the second electrode when a force is applied to the load transfer button.

5. The capacitive sensor of claim 4, further comprising a second conductive sheet on the second side of the insulating substrate, the second conductive sheet being electrically connected to the first conductive sheet wherein the first and second conductive sheets in combination with the second electrode and the conductive standoff are configured to form an electric shield about the first electrode.

6. The capacitive sensor of claim 4, wherein the second electrode comprises a central portion and at least one finger forming a spring mechanism, wherein the spring mechanism enables the central portion to move toward or away from the first electrode.

7. The capacitive sensor of claim 6, wherein the at least one finger is a plurality of fingers formed by a plurality of channels through the second electrode.

8. The capacitive sensor of claim 7, further comprising a tab that extends away from at least one of the plurality of fingers, and the tab secures the second electrode to the conductive standoff.

9. The capacitive sensor of claim 4, wherein the second electrode is symmetrical about two distinct axes.

10. The capacitive sensor of claim 4, further comprising electronic circuitry for determining a capacitance of a capacitor formed by the spaced relation of the first and second electrodes.

11. The capacitive sensor of claim 10, further comprising means for communicating with an external monitoring unit.

12. The capacitive sensor of claim 4, further comprising a deformable dielectric material positioned between the first electrode and the second electrode.

13. The capacitive sensor of claim 4, wherein the belt is configured to apply the force to the load transfer button.

14. A uterine contraction sensor configured to be secured to the abdomen of a patient, comprising:
- an insulating substrate;
- a first electrode disposed on a first side of the substrate;
- a second electrode positioned on the first side of the substrate in a spaced relation to the first electrode, at least part of the second electrode configured to move toward or away from the first electrode in response to a uterine contraction of the patient; and
- a conductive standoff sandwiched between the substrate and the second electrode for maintaining the second electrode in spaced relation to the first electrode, the conductive standoff electrically coupled to the second electrode and electrically isolated from the first electrode;
- a conductive sheet on each side of the substrate, wherein:
- the conductive sheets are electrically connected;
- the first electrode is electrically isolated from the conductive sheet on the first side of the substrate; and the second electrode is electrically connected to the conductive sheet on the first side of the substrate via the conductive standoff;
- wherein the conductive sheets in combination with the second electrode and the conductive standoff are configured to form an electric shield around the first electrode.

15. An extra-uterine sensing device, configured to be secured to an abdomen of a maternal patient to monitor a uterine contraction of the maternal patient, comprising:
- an insulating substrate having a first side and a second side;
- a first conductive sheet on the first side of the insulating substrate;
- a first electrode disposed on a first side of the substrate, the first electrode being electrically isolated from the first conductive sheet and the first electrode defines a first hole through the first electrode into the insulating substrate;
- a second electrode positioned above the first side of the insulating substrate in a spaced relation to the first electrode, at least part of the second electrode configured to move toward or away from the first electrode in response to the uterine contraction, the second electrode defines a second hole through second electrode;
- a conductive standoff sandwiched between the first conductive sheet and the second electrode, the conductive standoff maintains the spaced relation between the first and second electrodes, and the conductive standoff is electrically isolated from the first electrode;
- a load transfer button positioned on a side of the second electrode facing away from the first electrode; and
- a stem that extends from the load transfer button through the second hole in the direction of the first electrode, the stem is received at least partially within the first hole and the first hole guides the stem to prevent horizontal movement of the second electrode when a force is applied to the load transfer button.

16. The extra-uterine sensing device of claim 15 further comprising means for securing the extra-uterine sensing device against the abdomen of the maternal patient.

17. The extra-uterine sensing device of claim 15, further comprising a belt configured to secure the extra-uterine sensing device against the abdomen of the maternal patient.

* * * * *